United States Patent [19]
Müller et al.

[11] Patent Number: 6,074,547
[45] Date of Patent: Jun. 13, 2000

[54] PROCESS AND DEVICE FOR MEASURING THE OXYGEN POTENTIAL IN A SILICON MELT

[75] Inventors: Georg Müller, Langensendelbach; Albrecht Seidl, Erlangen, both of Germany

[73] Assignee: Wacker Siltronic Gesellschaft für Halbleitermaterialien AG, Burghausen, Germany

[21] Appl. No.: 09/134,850

[22] Filed: Aug. 14, 1998

[30] Foreign Application Priority Data

Aug. 21, 1997 [DE] Germany .............................. 197 36 469

[51] Int. Cl.[7] ................................................. G01N 27/407
[52] U.S. Cl. ............................................. 205/784; 204/422
[58] Field of Search ..................... 204/421, 422, 204/423; 205/783.5, 784

[56] References Cited

U.S. PATENT DOCUMENTS

| | | |
|---|---|---|
| 3,403,090 | 9/1968 | Tajiri et al. .............................. 204/422 |
| 3,794,569 | 2/1974 | Kawai et al. ............................ 204/422 |
| 4,313,799 | 2/1982 | Perkius . |
| 5,580,439 | 12/1996 | Baucke et al. . |
| 5,723,337 | 3/1998 | Müller et al. . |

FOREIGN PATENT DOCUMENTS

| | | |
|---|---|---|
| 0696652 | 8/1995 | European Pat. Off. . |
| 0635718 | 7/1996 | European Pat. Off. . |

OTHER PUBLICATIONS

R. Brückner; Properties and Structure of Vitreous Silica II, J. Non–Crystolline Solids 5 (1971), 177.

*Primary Examiner*—T. Tung
*Attorney, Agent, or Firm*—Collard & Roe, P.C.

[57] ABSTRACT

A process for measuring the oxygen potential in a silicon melt uses an electrochemical potential probe which dips into the melt. The probe voltage is measured using this potential probe which is made of an $SiO_2$ glass tube in which graphite is in direct contact with $SiO_2$ glass. The graphite has a wire making contact with it at the graphite upper end. The probe is dipped into the silicon melt only to an extent such that the graphite/wire contact point contained in the $SiO_2$ glass tube lies above the silicon melt.

6 Claims, 2 Drawing Sheets

PROCESS AND DEVICE FOR MEASURING THE OXYGEN POTENTIAL IN A SILICON MELT

BACKGROUND OF THE INVENTION

1. Field of the Invention

The invention relates to a process and to a device for measuring the oxygen potential in a silicon melt by means of an electrochemical potential probe which dips into the melt.

2. The Prior Art

In many processes for the production of electronic components with high packing density from silicon wafers, the amount of oxygen contained in the silicon is of great importance. The reason is that, in particular process steps, ever-increasing use is being made of the intrinsic getter action of oxygen. Therefore in microelectronics, monocrystalline silicon is exclusively used which has an oxygen content of about 0 atoms/cm$^3$.

Monocrystalline silicon is produced by Czochralski crucible pulling. During this pulling process the reaction between the silicon melt and the quartz crucible causes the melt to become enriched with oxygen. Oxygen is also incorporated into the growing crystal ingot. The melt oxygen concentration existing at the crystal growth boundary is also found in the crystal at about the same concentration.

However, the oxygen concentration in the melt changes during the pulling process due to the lowering melt level and the consequent reduction in the contact area between the melt and the quartz crucible. Furthermore, the thermal conditions which essentially influence the reaction between the crucible and the melt are not constant.

According to the prior art, infrared absorption measurements according to ASTM Standard F120/F121 are used to determine the oxygen content of a silicon ingot which has finished being pulled. This measurement is also used to compare this oxygen content with reference values. The parameters which affect the incorporation of oxygen are then corrected for the subsequent pulling process.

Those parameters which may influence the incorporation of oxygen in silicon ingots are the rotation of the crucible and/or of the crystal, the power with which the crucible is heated, the chamber pressure and the throughput of the inert gas flow:

1) the reaction between the silicon melt and the quartz crucible, and therefore the concentration of oxygen dissolved in the melt, can be controlled by increasing or decreasing the rotation of the crucible and/or of the crystal, and the power with which the crucible is heated,
2) the ratio between dissolved oxygen and SiO gas respectively in and above the melt can be controlled by varying the pressure in the chamber,
3) the concentration of SiO gas above the melt can be controlled by means of the throughput of the inert gas flow.

These parameters can only be corrected retrospectively, and not be used for a control loop. Thus, it is not possible for a uniform axial and radial oxygen distribution and a defined oxygen content to be achieved either over the entire crystal length or over several crystal ingots.

EP 0 696 652 A2 discloses an electrochemical potential probe for measuring the oxygen potentials in silicon melts. The probe consists of a sealed SiO$_2$ glass tube which contains a metal/metal oxide mixture and has a metal wire making contact with it. Transition metals, for example, Ti, V, Cr, Mn, Fe, Co and Ni are usually used as the reference mixture (metal/metal oxide).

The diffusion coefficients of these metals in quartz glass are up to 10$^{-4}$ cm$^2$/s at a temperature of 1420° C. (the melting temperature of Si) (R. Brückner; Properties and Structure of Vitreous Silica II, J. Non-crystalline Solids 5 (1971) 177).

When potential probes designed in this way are used for a fairly long time (>1 min), increased contamination of the melt by foreign metals must be expected. However, it is desirable to use a potential probe throughout the pulling process. This is because it is possible to make a control loop on the basis of the oxygen concentrations determined by measuring the oxygen potentials and by varying the parameters mentioned above.

SUMMARY OF THE INVENTION

It is an objective of the invention to provide a process, as well as a device for carrying out the process to determine the oxygen content of the melt by measuring the oxygen potential without causing contamination throughout the Czochralski (crucible) pulling process. The oxygen potential measurement value can also be used for a control loop which makes it possible to produce single silicon crystals with uniform axial and radial oxygen distribution.

The objective is achieved by a process for measuring an oxygen potential in a silicon melt comprising the steps of pulling a silicon single crystal from the silicon melt;

providing an electrochemical potential probe, said probe comprising a SiO$_2$ glass tube having a closed lower end and containing graphite having an upper end and being in direct contact with the SiO$_2$ glass tube and said probe having a wire making contact with the graphite at the upper end of the graphite; said contact occurring at a graphite wire contact point;

dipping said probe into the silicon melt only to a level such that graphite wire contact point contained in the SiO$_2$ glass tube is above the silicon melt;

measuring the voltage between the silicon melt and the wire contacting the probe caused by the difference between the melt oxygen potential and a reference oxygen potential in the probe; and determining the oxygen potential in the silicon melt from the probe voltage.

The object is further achieved by a device for measuring an oxygen potential in a silicon melt comprising an electrochemical potential probe dipped into the silicon melt, said potential probe comprising an SiO$_2$ glass tube containing graphite in direct contact with the SiO$_2$ glass; the graphite having an upper end; and a wire making contact with the graphite at the upper end.

The use of graphite in contact with SiO$_2$ glass for producing a reference oxygen potential in the process according to the invention has a number of advantages. The total number of materials involved in the crucible pulling process is reduced to a minimum. Thus only carbon, silicon and oxygen are found in the critical region of the melt. Carbon will enter the melt via the graphite support crucible through the quartz crucible, and via the atmosphere which contains CO. Nevertheless, it is known to the person skilled in the art that, due to its electronic properties, carbon incorporated in silicon single crystals does not impair quality in the same way as foreign metals do.

The wire making contact with the graphite at its upper end is excluded as a source of foreign metal contamination. This is because the contact point lies above the region of the probe which dips into the melt.

BRIEF DESCRIPTION OF THE DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

Figure 1:
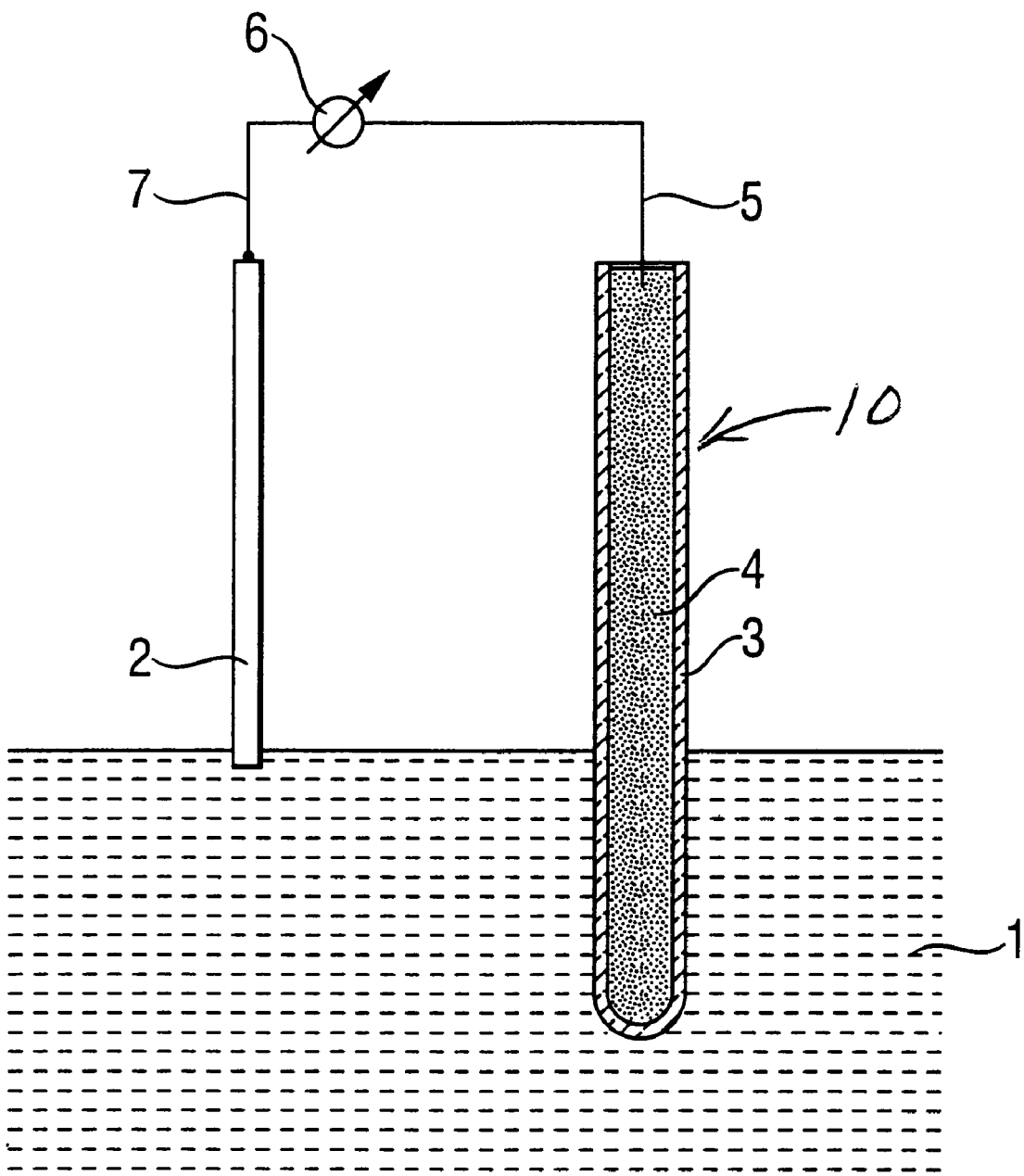
FIG. 1 shows a device for performing the process of the invention.

Turning now in detail to the drawings, FIG. 1 shows an essential component of the device according to the invention which is the electrochemical potential probe 10. Probe 10 includes an $SiO_2$ glass tube 3 containing graphite 4 which is in direct contact with $SiO_2$ glass and has a wire 5 making contact with the graphite upper end. A melt contact 2, for example a crystal ingot being grown from the silicon melt 1, is dipped together with the potential probe 10, into the silicon melt 1. The melt contact 2 has a wire 7 making contact with it and, like the wire 5 of the potential probe, is electrically connected to the voltmeter 6.

A defined temperature-dependent reference oxygen potential is formed at the boundary between the $SiO_2$ glass tube 3 and the graphite 4 adjoining it.

It has been found that, by using the $SiO_2$ glass and graphite in the probe of the invention, the probe voltage can be exactly measured and will remain stable over a long time. Further, there was no contamination of the silicon melt by foreign metals.

In conventional electrochemical potential probes, which consist for example, of zirconia tube containing a metal/metal oxide, exists the danger at a contamination of the silicon melt and the silicon single crystal by the metals from the metal/metal oxide reference mixture and by or in the example of a zirconia electrolyte.

In the device of the invention, wire 5 and wire 7 are composed of the same metal or metal alloy such as titanium, tungsten or molybdenum. Thus the reference oxygen potential is formed exclusively by the $SiO_2$/graphite combination and therefore can be measured exactly. The $SiO_2$ glass tube 3 is itself involved in the creation of the reference oxygen potential and, thus is a solid electrolyte.

The oxygen content or mol fraction $n_0$ in the silicon melt is calculated from the equation $$n_0 = \sqrt{p_r} \exp\left(\frac{-2UF(-\Delta G^0)}{RT}\right)$$

with U being the probe voltage, F being Faraday's constant, R being the gas constant, T being the temperature of the silicon melt, $p_r$ being the reference partial pressure and $\Delta G^0$ being free enthalpy of solution of oxygen in a silicon melt. The probe voltage U and the temperature T are measured; all the other parameters are constant or can be determined with the aid of known measuring techniques.

Figure 2:
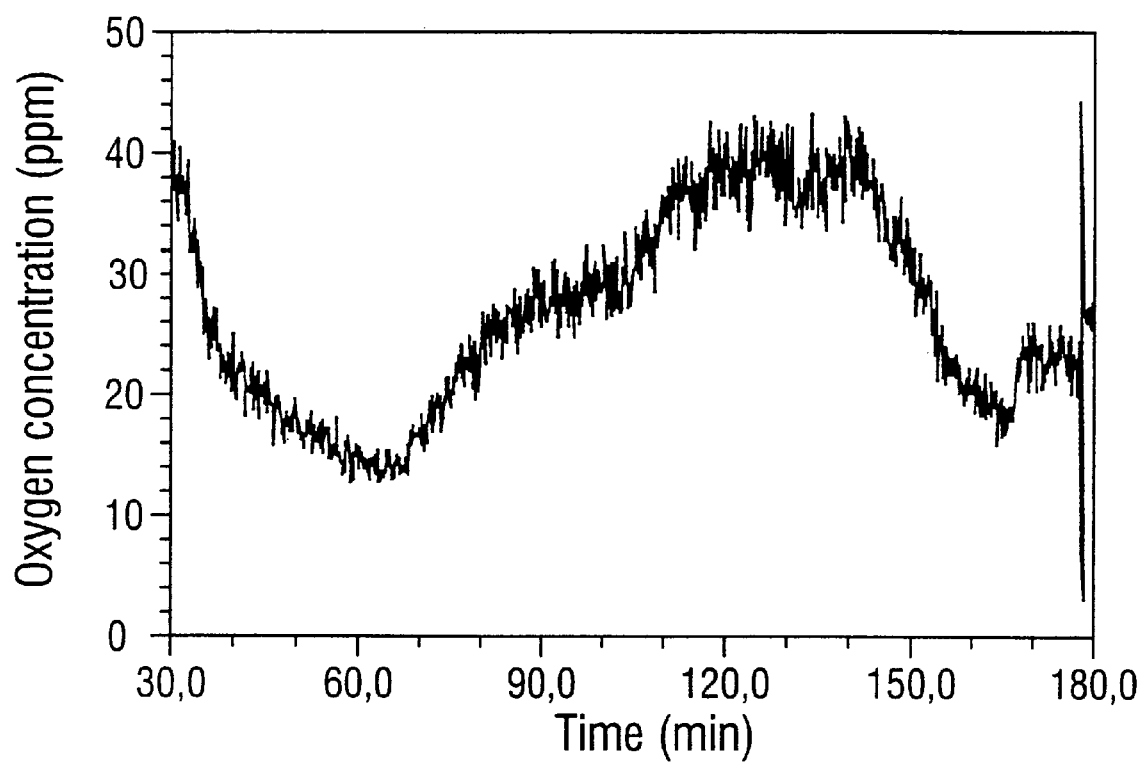
FIG. 2 shows the oxygen content of the silicon melt which is determined by using the device shown in FIG. 1.

FIG. 2 shows the oxygen concentration in a silicon melt determined using the device of FIG. 1 during a time period of 180 min.

The power used to heat the crucible was varied during the experiment. This led to a change in the oxygen solubility for the melt in the crucible, and therefore to a variation in the oxygen concentration in the melt. The measured variation in the oxygen concentration correlates with these expectations. When the process is used in a control loop for setting a particular oxygen concentration, then further variables are adjusted in addition to varying the power used to heat the crucible. These other variables include the rotation of the crucible and/or of the crystal, the pressure in the chamber and the throughput of the inert gas flow, and combinations of these variables.

By using the process and the device of the invention, the oxygen concentration in a silicon melt can be determined without causing contamination throughout the Czochralski (crucible) pulling process. These measurements, and regulation of the parameters by which the incorporation of oxygen can be influenced, permit the production of silicon single crystals. These crystals have a uniform axial and radial oxygen distribution.

While a few embodiments of the present invention have been shown and described, it is to be understood that many changes and modifications may be made hereunto without departing from the spirit and scope of the invention as defined in the appended claims.

What is claimed is:

1. A process for measuring an oxygen potential in a silicon melt comprising the steps of pulling a silicon single crystal from the silicon melt;

providing an electrochemical potential probe, said probe comprising a $SiO_2$ glass tube having a closed lower end and containing graphite having an upper end and being in direct contact with the $SiO_2$ glass tube and said probe having a wire making contact with the graphite at the upper end of the graphite; said contact occurring at a graphite/wire contact point;

dipping said probe into the silicon melt only to a level such that the graphite/wire contact point contained in the $SiO_2$ glass tube is above the silicon melt;

measuring the voltage between the silicon melt and the wire contacting the probe caused by the difference between the melt oxygen potential and a reference oxygen potential in the probe; and determining the oxygen potential in the silicon melt from the probe voltage.

2. The process as claimed in claim 1, wherein silicon dioxide of the $SiO_2$ glass tube is used in combination with graphite to form the reference oxygen potential and, simultaneously to form a solid electrolyte.

3. The process as claimed in claim 1, wherein another wire is connected to said silicon single crystal; and connecting a voltmeter between said wire connected to the graphite and said another wire connected to said silicon single crystal for measuring said voltage of the probe.

4. A device for measuring an oxygen potential in a silicon melt comprising a silicon melt;

an electrochemical potential probe dipped into the silicon melt; said potential probe comprising a $SiO_2$ glass tube containing graphite in direct contact with $SiO_2$ glass;

said graphite having an upper end; and a wire making contact with said graphite at a point at said upper end, said graphite/wire contact point being above the silicon melt.

5. The device as claimed in claim 4, wherein said $SiO_2$ glass tube has an inner wall in contact with the graphite.

6. The device as claimed in claim 4, wherein another wire is connected to a silicon single crystal which contacts said melt; and a voltmeter is connected between said wire connected to the graphite and said another wire connected to said silicon single crystal for measuring voltage of the probe.

* * * * *

UNITED STATES PATENT AND TRADEMARK OFFICE
CERTIFICATE OF CORRECTION

PATENT NO. : 6,074,547
DATED : June 13, 2000
INVENTOR(S) : MÜLLER ET AL

It is certified that error appears in the above-identified patent and that said Letters Patent is hereby corrected as shown below:

On the title page, column 1, Item [75], change the city of the second inventor from "Erlangen" to:

--Freiberg--.

Signed and Sealed this

Seventeenth Day of April, 2001

NICHOLAS P. GODICI

Attest:

Attesting Officer

Acting Director of the United States Patent and Trademark Office